(12) United States Patent
Hoffman et al.

(10) Patent No.: US 6,565,564 B2
(45) Date of Patent: May 20, 2003

(54) MULTI-PIN CLAMP AND ROD ATTACHMENT

(75) Inventors: Mindy Lynn Hoffman, Pottstown, PA (US); Charles Dean Preston, II, Fort Walton Beach, FL (US); Michael Charles Mazzio, Schwenksville, PA (US)

(73) Assignee: Synthes U.S.A., Paoli, PA (US)

( * ) Notice: Subject to any disclaimer, the term of this patent is extended or adjusted under 35 U.S.C. 154(b) by 92 days.

(21) Appl. No.: 09/736,753

(22) Filed: Dec. 14, 2000

(65) Prior Publication Data

US 2002/0077629 A1 Jun. 20, 2002

(51) Int. Cl.⁷ .................................................. A61F 5/04
(52) U.S. Cl. ...................................................... 606/59
(58) Field of Search ............................ 606/54, 57, 58, 606/59

(56) References Cited

U.S. PATENT DOCUMENTS

| | | |
|---|---|---|
| 1,997,466 A | 4/1935 | Longfellow |
| 2,250,417 A | 7/1941 | Ettinger |
| 2,346,346 A | 4/1944 | Anderson |
| 2,391,537 A | 12/1945 | Anderson |
| 2,391,693 A | 12/1945 | Ettinger |
| 4,135,505 A | 1/1979 | Day |
| 4,271,832 A | 6/1981 | Evans et al. |
| 4,312,336 A | 1/1982 | Danieletto et al. |
| 4,365,624 A | 12/1982 | Jaquet |
| 4,483,334 A | 11/1984 | Murray |
| RE31,809 E | 1/1985 | Damieletto et al. |
| 4,502,473 A | 3/1985 | Harris et al. |
| 4,535,763 A | 8/1985 | Jaquet |
| 4,541,422 A | 9/1985 | de Zbikowski |
| 4,620,533 A | 11/1986 | Mears |
| 4,621,627 A | 11/1986 | DeBastiani et al. |
| 4,628,919 A | 12/1986 | Clyburn |
| 4,628,922 A | 12/1986 | Dewar |
| 4,714,076 A | 12/1987 | Comte et al. |
| 4,922,896 A | 5/1990 | Agee et al. |
| 4,941,481 A | 7/1990 | Wagenknecht |
| 4,988,349 A | 1/1991 | Pennig |
| 5,053,034 A | 10/1991 | Olerud |
| 5,098,432 A | 3/1992 | Wagenknecht |
| 5,108,394 A | 4/1992 | Kurokawa et al. |
| 5,152,280 A | 10/1992 | Danieli |
| 5,160,335 A | 11/1992 | Wagenknecht |
| 5,207,676 A | 5/1993 | Canadell et al. |
| 5,219,349 A | 6/1993 | Krag et al. |
| 5,292,322 A | 3/1994 | Faccioli et al. |
| 5,320,622 A | 6/1994 | Faccioli et al. |
| 5,320,623 A | 6/1994 | Pennig |
| 5,342,360 A | 8/1994 | Faccioli et al. |
| 5,376,090 A | 12/1994 | Pennig |

(List continued on next page.)

FOREIGN PATENT DOCUMENTS

| | | |
|---|---|---|
| DE | 299 22 734 U1 | 3/2000 |
| WO | WO/0038585 | 7/2000 |

*Primary Examiner*—Eduardo C. Robert
(74) *Attorney, Agent, or Firm*—Pennie & Edmonds LLP

(57) ABSTRACT

The present invention provides a simplified external bone fixator assembly which allows the surgeon to snap the assembly onto a bone fixation rod at an intermediate location along the length of the rod. It is not necessary to "thread" the assembly onto the rod starting at the end and sliding it down the length of the rod to the desired location. In particular, this invention provides a novel bone pin locking assembly for use with standard bone fixation rods, and bone pins. The bone pin locking assembly includes a bone pin vise, a single-piece fixation rod clamp, and a coupling to allow relative adjustment of the pin vise and the rod clamp. The rod clamp is a single-piece construction, having a jaw capable of loosely capturing the bone fixation rod when the surgeon presses the jaw onto the rod. The assembly may be rigidly fixed to the rod using a bolt which tightens the jaw onto the rod.

32 Claims, 8 Drawing Sheets

U.S. PATENT DOCUMENTS

| | | |
|---|---|---|
| RE34,985 E | 6/1995 | Pennig |
| 5,454,810 A | 10/1995 | Pohl et al. |
| 5,624,440 A | 4/1997 | Huebner |
| 5,630,815 A | 5/1997 | Pohl et al. |
| 5,658,283 A | 8/1997 | Huebner |
| 5,662,648 A | 9/1997 | Faccioli et al. |
| 5,662,650 A | 9/1997 | Bailey et al. |
| 5,683,389 A * | 11/1997 | Orsak .......................... 606/59 |
| 5,709,681 A | 1/1998 | Pennig |
| 5,728,096 A | 3/1998 | Faccioli et al. |
| 5,752,954 A | 5/1998 | Mata et al. |
| 5,788,695 A | 8/1998 | Richardson |
| 5,827,282 A | 10/1998 | Pennig |
| 5,827,283 A | 10/1998 | Groiso et al. |
| 5,891,144 A | 4/1999 | Mata et al. |
| 5,921,985 A | 7/1999 | Ross, Jr. et al. |
| 5,941,879 A | 8/1999 | Walulik et al. |
| 5,954,725 A | 9/1999 | Sherman et al. |
| 6,022,348 A | 2/2000 | Spitzer |
| 6,024,745 A | 2/2000 | Faccioli et al. |
| 6,277,119 B1 * | 8/2001 | Walulik et al. ............... 606/57 |

* cited by examiner

MULTI-PIN CLAMP AND ROD ATTACHMENT

TECHNICAL FIELD

The present invention relates to a traumatologic device, and, more particularly, to an improved traumatologic device for reducing long-bone fractures that require external fixation.

BACKGROUND OF THE INVENTION

A variety of traumatologic devices for reduction of bone segments are known in the art. For example external bone fixation devices (commonly referred to as external fixators) are known. Typically external fixators are used to reduce fractures of the long bones in the human body. These devices are always placed in position under anesthesia. In order to reduce the duration of the anesthesia, fixator devices have been developed to allow positioning at every possible angle, while still allowing easy adjustment by a surgeon.

The early development of external fixator devices, such as that exemplified by U.S. Pat. No. 2,250,417 to Ettinger, was aimed at producing a simple and lightweight fracture reduction device which is practical to leave in place to serve as a retention device, thereby rendering a cast unnecessary. As disclosed, the Ettinger device allows two separate sets of dual bone pins or screws, each transcutaneously installed in the bone on either side of a fracture, to be connected and fixed at variable points to a single bone fixation rod running roughly parallel to the longitudinal axis of the affected bone. This resultant connection of opposing pin/screw sets provides the immobilization necessary to allow proper healing of the fracture. Ettinger discloses the use of multiple sleeve and post connections between the bone pins/screws and the bone fixation rod to allow the bone pins or screws to be installed at varying angles relative to the bone fixation rod. Ettinger additionally discloses the use of a rod and sleeve configuration whereby one of the two bone pin/screw couplings is fixed to the bone fixation rod, while the second comprises an internally threaded sleeve that is threaded over the opposite end of the bone fixation rod, and whose position is adjustable relative to the fixed coupling via rotation of the bone fixation rod.

Later improvements on the Ettinger design, such as that disclosed by U.S. Pat. No. 4,135,505 to Day, allow for the installation of an increased and/or variable number of bone pins on each side of the fracture. This provides the advantage of giving the practitioner more options in the spacing of pins, and of avoiding installing a pin at a particular point on the bone if such placement was undesirable. The Day device additionally discloses a bone pin clamp incorporating a ball and socket connection to allow for varying bone pin installation angles.

Further improvements such as those disclosed by U.S. Pat. No. 5,160,335 to Wagenknecht, U.S. Pat. No. 5,219,349 to Krag, U.S. Pat. No. 5,624,440 to Huebner, U.S. Pat. No. 5,891,144 to Mata et al., and U.S. Pat. No. 6,022,348 to Spitzer disclose bone pin/screw clamps which incorporate more modern universal joint assemblies to allow easier adjustment of the distance between bone pin clamps along the length of the bone fixation rod when the attached bone pins/screws are installed at multiple angles relative to the immobilization rod. Moreover the Krag, Huebner, Mata et al., and Spitzer devices provide easier means to adjust the relative distance between bone pin couplings on opposing sides of a fracture (accomplished by simple sliding in the Krag, Huebner, Mata et al., and Spitzer devices, and by incremental rotation of an attached screw and nut combination in the Day and Wagenknecht devices). Yet a further improvement is disclosed in the Wagenknecht patent, which provides springs between the bone pin clamp faces to spread the faces and thereby facilitate introduction of the bone pins.

The difficulty with the Huebner, Krag, Wagenknecht and Day devices is that their means of fixing the bone pin clamp to the bone fixation rod is by way of a closed hole and screw combination. To facilitate installation of these fixators, the bone pin clamps must be threaded onto the bone fixation rod from one end of the rod, making installation cumbersome. The Mata et al., and Spitzer devices address this problem by providing bone pin clamps that attach to the bone fixation rod utilizing open-face jaws. This design allows the device to be engaged with the rod by simply placing it onto the desired location along the length of the rod, without the need for threading as in the Mata et al. and Spitzer devices. The difficulty with the Mata et al. and Spitzer devices is that their open-faced bone pin clamp jaws are two-piece designs which by their nature cannot be self-sprung and so require the use of an additional piece, such as a coil or compression spring, to maintain the jaws in an open position during installation onto the bone fixation rod. Additionally, the two piece nature of their design increases unit fabrication difficulty and cost.

Accordingly, there is a need in the art to provide a simpler design bone pin clamp assembly that minimizes the total number of steps an operator must take to engage the clamp assemblies and bone fixation rod, while still providing maximum flexibility to the operator in adjusting the distance between bone pin clamps on either side of a fracture.

SUMMARY OF THE INVENTION

The present invention addresses the need in the art by providing a bone fixation rod attachment assembly which allows a surgeon to snap the assembly onto one or more bone fixation rods, to provide loose capture of the rod in a minimum number of steps, and with a minimum of attention, and while retaining the flexibility of providing for the locking of multiple bone pins installed at multiple angles, on opposite sides of a fracture.

In particular, the present invention provides an external fixator for reducing fragments of a bone, comprising a bone fixation rod, at least two sets of bone pins, and a bone pin locking assembly comprising a pin vise, a bone fixation rod attachment portion having a single-piece fixation rod clamp, and a coupling to provide relative rotation in two axes between the pin vise and the fixation rod attachment portion. The single piece fixation rod clamp comprises a jaw portion which permits engagement of the bone fixation rod when the single-piece fixation rod clamp is pressed onto the bone fixation rod from the side of the bone fixation rod. This action loosely couples the bone pin locking assembly to the bone fixation rod. This loose coupling may be achieved by providing the single-piece fixation rod clamp with a jaw portion, having first and second opposing jaws, the clearance between these jaws being slightly smaller than the outside diameter of the bone fixation rod. An interference is thereby established between the single-piece fixation rod clamp jaw and the bone fixation rod when the rod is initially installed into the jaw. The first and second opposing jaws further connect to adjoining spring arms, which themselves converge into a single cylindrical coupling end. When the first and second opposing jaws are positively displaced with respect to their rest position, a resulting spring force is generated which tends to force the jaws back to their rest position. In this way, the bone fixation rod may be snapped into the jaw portion by the surgeon applying the requisite pressure.

The present invention also provides for the immobilization of the bone pin locking assembly along the bone fixation rod so the locking assembly may neither move nor rotate. This may be achieved by the use of a bolt disposed between the opposing jaws of the single-piece fixation rod clamp jaw portion. Immobilization occurs through the tightening of the bolt, which draws the jaws together to a final, locked, position.

The present invention also enables the bone pin locking assembly to engage the bone fixation rod by pressing the single-piece fixation rod clamp into the bone fixation rod in a direction substantially along the rod clamp longitudinal axis, or in a direction substantially perpendicular to the bone fixation rod longitudinal axis.

The present invention further provides cooperating serrations on the bearing faces of the pin vise portion and the single-piece fixation rod clamp coupling. These serrations serve to prevent relative rotational movement between the single piece fixation rod clamp and the pin vise upon final tightening of a coupling bolt. The present invention additionally provides a spring, located between the serrated bearing faces of the pin vise portion and the single-piece fixation rod clamp coupling. This spring provides a force tending to separate the coupling and the pin vise portion to allow free relative rotational movement between the two pieces prior to final tightening of the coupling bolt, or subsequent to loosening of the coupling bolt.

The present invention further provides grooves in the pin vise clamping faces that captivate the bone pins when the engaging faces are clamped together. These clamping grooves may be of cylindrical, or generally arcuate, cross section, or they may be of triangular cross section. In any case the grooves in each clamping face are designed to contact the bone pins along less than 180 degrees of the circumference of each bone pin.

The present invention also provides a method for treating a fractured bone, comprising the insertion of at least two sets of bone pins into the bone on opposite sides of a fracture, and installing on those bone pins first and second bone pin locking assemblies each comprising a pin vise portion, and a rod attachment portion comprising a rotatable coupling and a single-piece fixation rod clamp. The pin vise portion of the first bone pin locking assembly engages at least one bone pin on the first side of the fracture, and the pin vise portion of the second bone pin locking assembly engages at least on bone pin on the second side of the fracture. The jaw portion of each single-piece fixation rod clamp is then snapped onto a bone fixation rod along a direction perpendicular to the longitudinal axis of the fixation rod. Each bone pin locking assembly is then adjusted to its final position and orientation, whereupon the assemblies are immobilized along the bone fixation rod. The present invention further provides for this immobilization by the tightening of a bolt disposed within the bone pin locking assembly jaw portion.

In particular, the treatment method of the present invention may be utilized for consolidation of bone portions, where the opposing portions of fractured bones are forced together prior to immobilization. The present invention may also be utilized to facilitate distraction of opposing segments of bone, so as to permit osteosynthesis in the region between the opposing bone segments.

The features and advantages of the present invention will become more readily apparent from the following detailed description of the invention in which like elements are labeled similarly and in which.

DETAILED DESCRIPTION OF THE PREFERRED EMBODIMENTS

The traumatological device of the present invention is discussed herein with reference to a preferred embodiment adapted to be used in the consolidation and fixation of a fractured long bone. It is to be understood that the invention finds applicability for use in any circumstance in which it is desired to fix the orientation of bone segments on either side of a fracture.

Figure 1A:
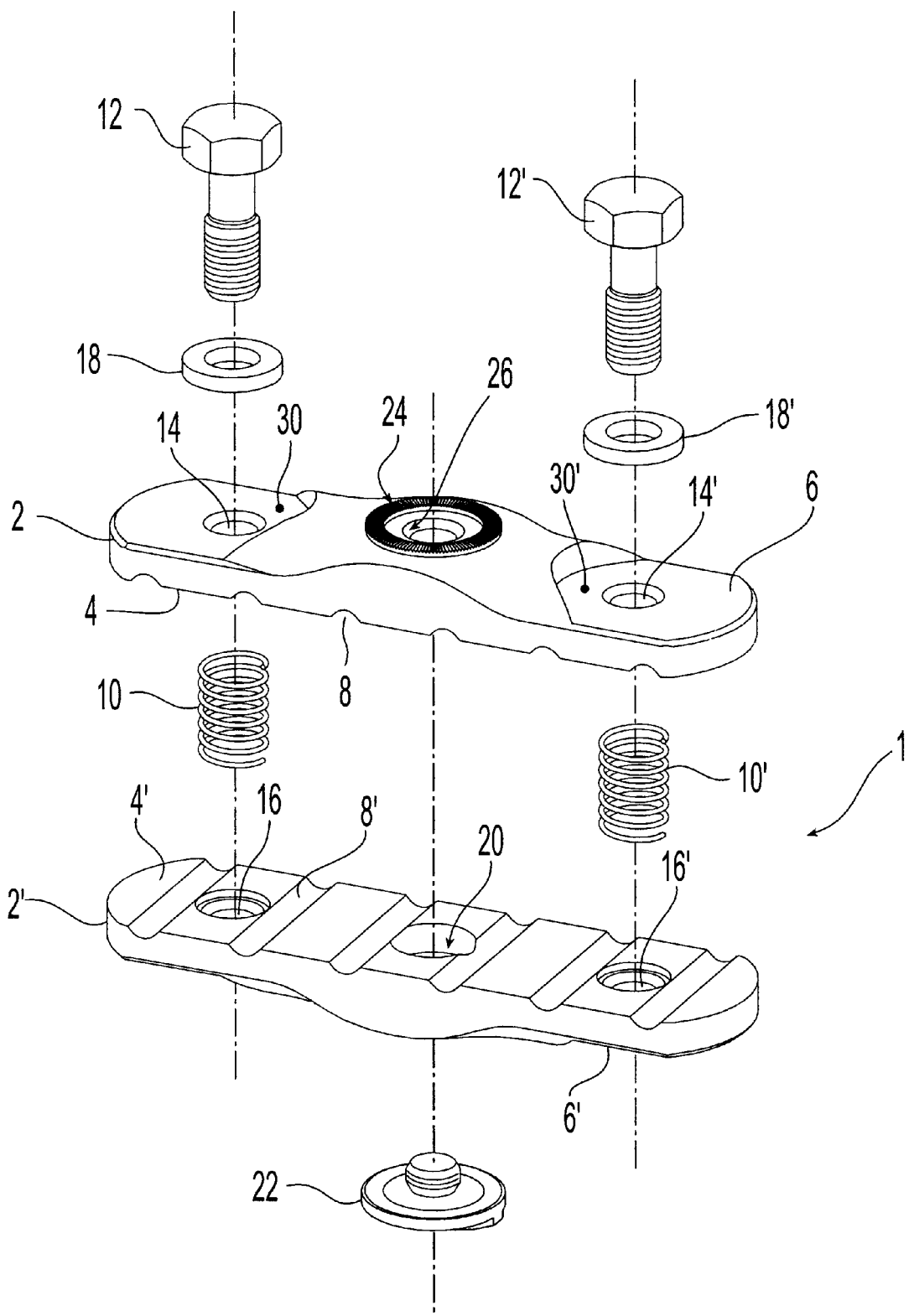
FIGS. 1A, 1B and 1C are two exploded perspective views and an elevation view of a bone pin vise portion, a bone pin vise opposing plate and star grind cover, and a bone pin vise opposing plate incorporating triangular bone pin clamping grooves, respectively, of the bone pin locking assembly of the current invention.
Figure 6:
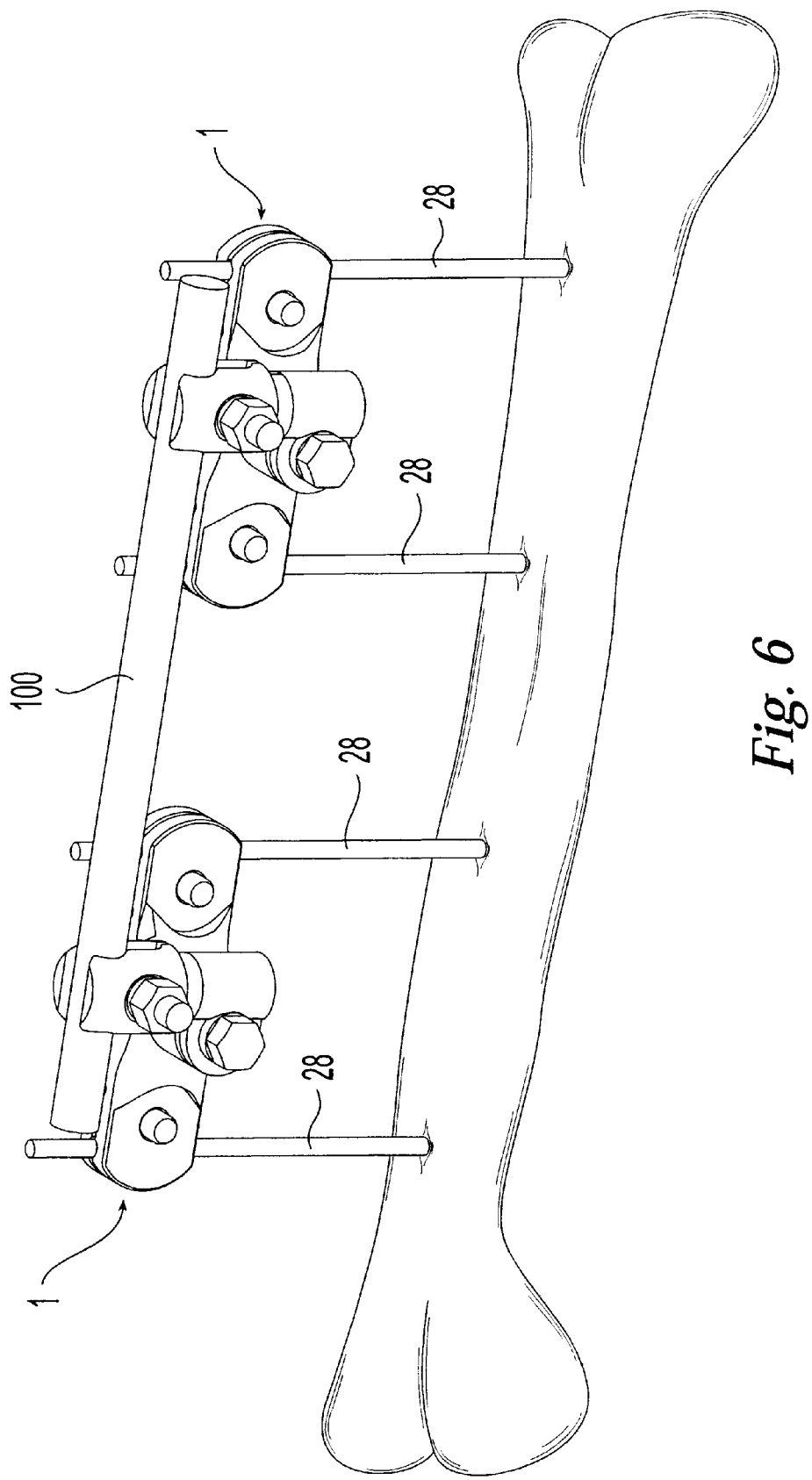
FIG. 6 is a perspective view of a complete bone fixation device installed on a bone.

Referring more particularly to the drawings, FIG. 1A shows an exploded view of a bone pin vise portion. As shown in FIG. 1A, the bone pin vise portion 1 comprises first and second opposing plates 2 and 2' with engaging faces 4 and 4', and outside faces 6 and 6'. Each engaging face is characterized by a plurality of spaced parallel grooves 8 and 8' which are cylindrically arcuate and which are in confronting relation to the spaced parallel grooves on the face of the opposite plate. The parallel grooves 8 and 8' coordinate to receive the proximal ends of bone pins 28 (shown in FIG. 6) installed on one side of a fractured bone. When the pin vise portion is in the clamped condition, the bone pins 28 are nested in the respective grooves formed by the conjunction of parallel grooves 8 and 8' (of engaging faces 4 and 4'). It will be understood that the number and shape of the grooves is not critical to the operation of the device.

The opposing plates 2 and 2' are connected by two vise bolts 12 and 12' which operate to draw together engaging faces 4 and 4' in order to grip the proximal ends of bone pins 28 which have been installed in a bone. Vise bolts 12 and 12' are slideably accepted by corresponding bores 14 and 14' in each end of first opposing plate 2, and are threadably accepted by threaded bores 16 and 16' in each end of second opposing plate 2'. The internal threads of bores 16 and 16' of second opposing plate 2' correspond with the external threads of vise bolts 12 and 12' such that a clockwise rotation of vise bolts 12 and 12' acts to draw opposing plates 2 and 2', and therefore engaging faces 4 and 4', together. Further, first opposing plate 2 incorporates bolt head bearing surfaces 30 and 30' to provide uniform bearing contact with the bottoms of the heads of pin vice bolts 12 and 12'. The vise bolts 12 and 12' may be provided with washers 18 and 18' positioned between the heads of the vice bolts 12 and 12', and bolt head bearing surfaces 30 and 30' of the pin vise portion opposing plate 2. The washers serve to reduce friction between the vise bolts and bolt head bearing surfaces, thereby easing final tightening of the vise bolts.

Preferably, the vise bolts 12 and 12' will be initially fit with the washers 18 and 18', then installed in the opposing plates, followed by a "loose-fit" tightening to the point that only a small clearance remains between the cylindrical voids formed by the plurality of spaced parallel grooves 8 and 8' and the outside surfaces of the cylindrical bone pins 28. In this way the pin vise portion 1 may easily be slipped onto the bone pins 28, such that during the surgical procedure only minor additional tightening of the vise bolts 12 and 12' will be required to firmly fix the bone pins 28 within the bone pin vise portion 1.

Figure 3:
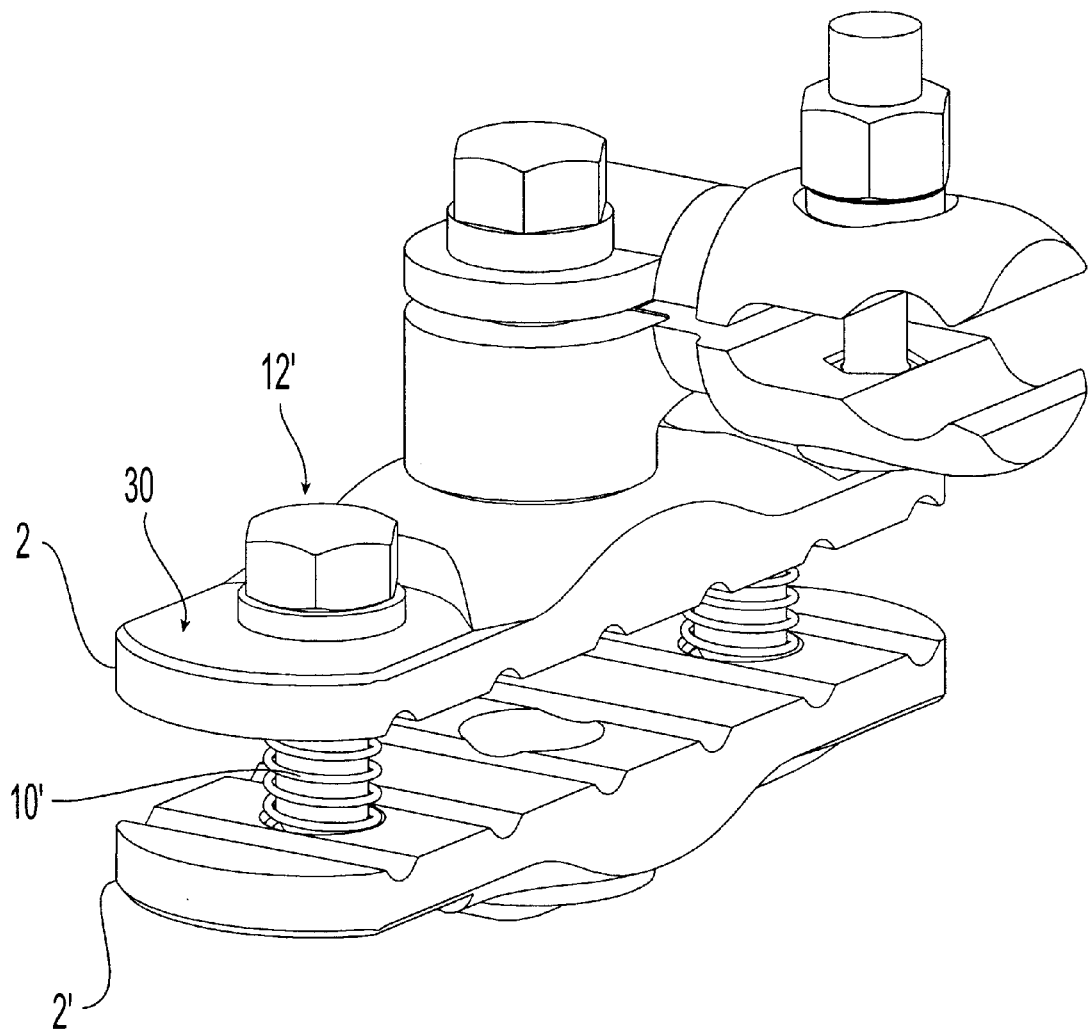
FIG. 3 is a perspective view of an assembled bone pin vise portion of FIG. 1 connected to an assembled rod attachment portion of FIG. 2.

In a preferred embodiment, the pin vise portion opposing plates 2 and 2' incorporate coil springs 10 and 10' between engaging faces 4 and 4' to forcibly separate engaging faces 4 and 4'. The provision of this separating force holds the plates apart during installation of the pin vise portion onto the bone pin proximal ends, easing such installation. To this end, cylindrical coil springs 10 and 10' are installed about the shafts of vise bolts 12 and 12' such that vise bolt shafts are slidably received by the bore formed within the inside diameter of each coil spring 10 and 10' (see FIG. 3).

Figure 2:
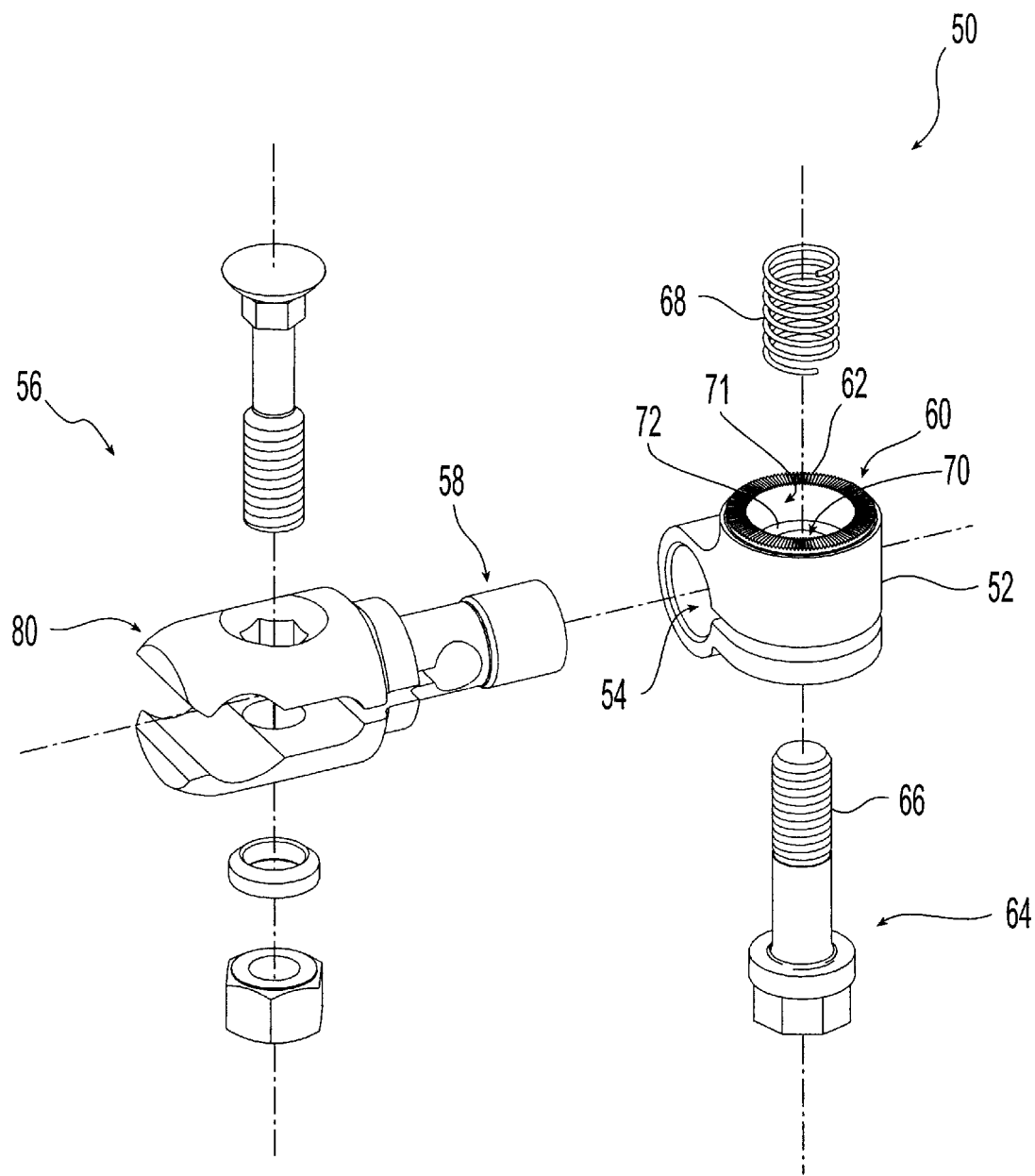
FIG. 2 is an exploded perspective view of a rod attachment portion of the bone pin locking assembly of the current invention.

FIG. 2 shows an exploded view of a rod attachment portion 50, comprising a single-piece fixation rod clamp 56, a coupling 52, a coil spring 68, and a coupling bolt 64. The single-piece fixation rod clamp has a cylindrical coupling portion 58 which is slidably disposed within an aperture 54 formed by the body of the coupling 52. Single-piece fixation rod clamp 56 is thus interconnected to and slidably disposed within the coupling 52 so as to allow 360-degree rotation of the single-piece fixation rod clamp 56 within the coupling aperture 54. The coupling bolt 64, having a head and a threaded distal end 66, is slidably disposed within a bore 70 formed in the body of coupling 52. The longitudinal axis of bore 70 is oriented perpendicular to that of the coupling aperture 54. The coupling bolt threaded distal end 66 is threadably accepted by an internally and compatibly threaded bore 26 formed in the top center of opposing plate 2 (shown in FIG. 1A) of pin vise portion 1 (shown in FIG. 1A). The single-piece fixation rod clamp 56 is thus interconnected to and rotatably disposed about pin vise portion 1. The single-piece fixation rod clamp 56 is interconnected to and rotatably disposed, with two degrees of rotational freedom, about pin vise portion 1, and so about bone pins 28 (shown in FIG. 6). The first degree of rotational freedom is provided by the rotation of single-piece fixation rod clamp 56 relative to the rod attachment portion coupling 52; the second by the rotation of the rod attachment portion coupling relative to pin vise portion 1.

The single-piece fixation rod clamp 56 is stabilized and fixed to the rod attachment portion coupling 52 by tightening the coupling bolt 64. Tightening of the coupling bolt 64 also results in the stabilization and fixation of the entire rod attachment portion 50 to the pin vise portion 1.

In a preferred embodiment, the coupling 52 has a bearing face 60 incorporating serrations 62 which extend over the entire face, and which correspond with like serrations 24 (shown in FIG. 1A) formed in the corresponding bearing face of the pin vise portion 1. The serrations may be disposed in a radial fashion to form a "star grind," or may have any type of profile known in the art. The serrations 62, 24 serve to minimize or prevent rotational slippage between the coupling 52 and the pin vise portion 1 subsequent to final tightening of the coupling bolt 64.

Figure 1B:
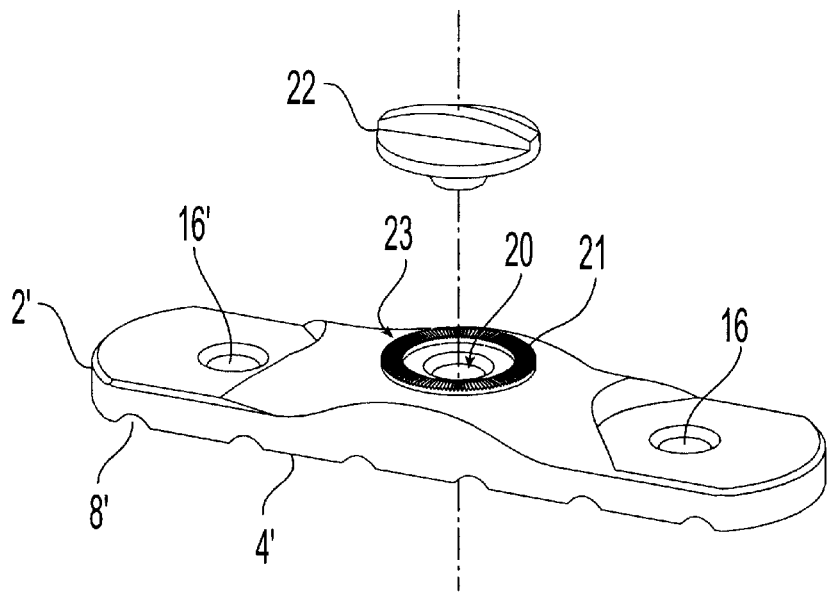
Figure 1C:
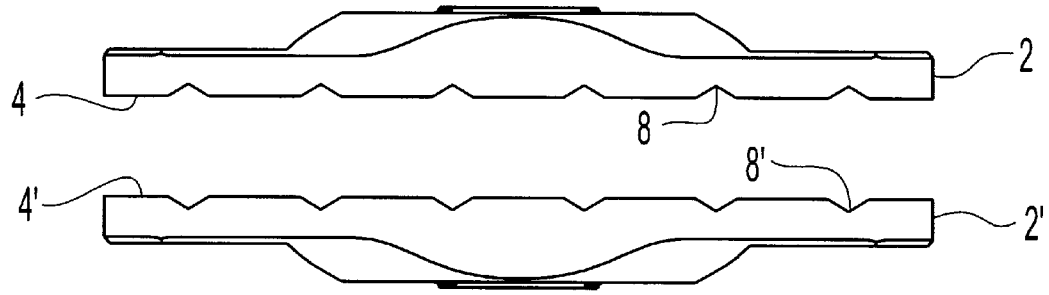

In another preferred embodiment, the pin vise portion opposing plate 2' (shown in FIG. 1B) incorporates an internally threaded bore 20, into which the coupling bolt 64 of a second rod attachment portion 50 (shown in FIG. 2) may be threaded. The bearing face 21 of the pin vise portion opposing plate 2' incorporates serrations 23 which extend over the entire face, and which correspond with like serrations 62 of the bearing face 60 of a second rod attachment portion 50 (shown in FIG. 2). The serrations 62, 23 serve to minimize or prevent rotational slippage between the second coupling 52 and the pin vise portion 1 subsequent to final tightening of the second coupling bolt 64. Two rod attachment portions 50 may thereby be installed on one pin vise portion 1 to provide the fracture site with the additional stabilizing force of a second bone fixation rod 100 (shown in FIG. 6). For those instances in which the surgeon does not require the additional stabilizing force of a second bone fixation rod, an externally threaded "star grind" cover 22 (shown in FIGS. 1A and 1B) is provided. The cover is threadably accepted by the internally threaded bore 20 of the pin vise portion opposing plate 2' (shown in FIGS. 1A and 1B). The cover 22 may have a bearing face 25 (shown in FIG. 1A) incorporating serrations 27 which extend over the entire face, and which correspond with like serrations 23 (shown in FIG. 1B) formed in the corresponding bearing face of the pin vise portion opposing plate 2'. The serrations may be disposed in a radial fashion to form a "star grind," or may have any type of profile known in the art. The serrations 23, 27 serve to minimize or prevent rotational slippage between the star grind cover 22 and the pin vise portion 1 subsequent to final tightening of the star grind cover.

As shown in FIG. 2, the coupling bolt 64 may be provided with a coil spring 68 disposed about the circumference of the bolt 64. The spring is partially slidably received within a bore 71 provided in the coupling bearing face 60. This bore is of larger diameter than coupling bore 70, which results in the creation of a circumferential ledge 72 within the coupling 52. When compressed between the rod attachment portion coupling circumferential ledge 72 and the pin vise portion 1 (shown in FIG. 1A), the spring 68 acts to provide a force tending to separate the coupling 52 and the pin vise portion 1. This force prevents engagement of the serrations 62, 24 (and serrations 62, 23 in the alternative embodiment where a second bone fixation rod is utilized) during installation, and thus enables easy relative rotation and fit-up.

Figure 4:
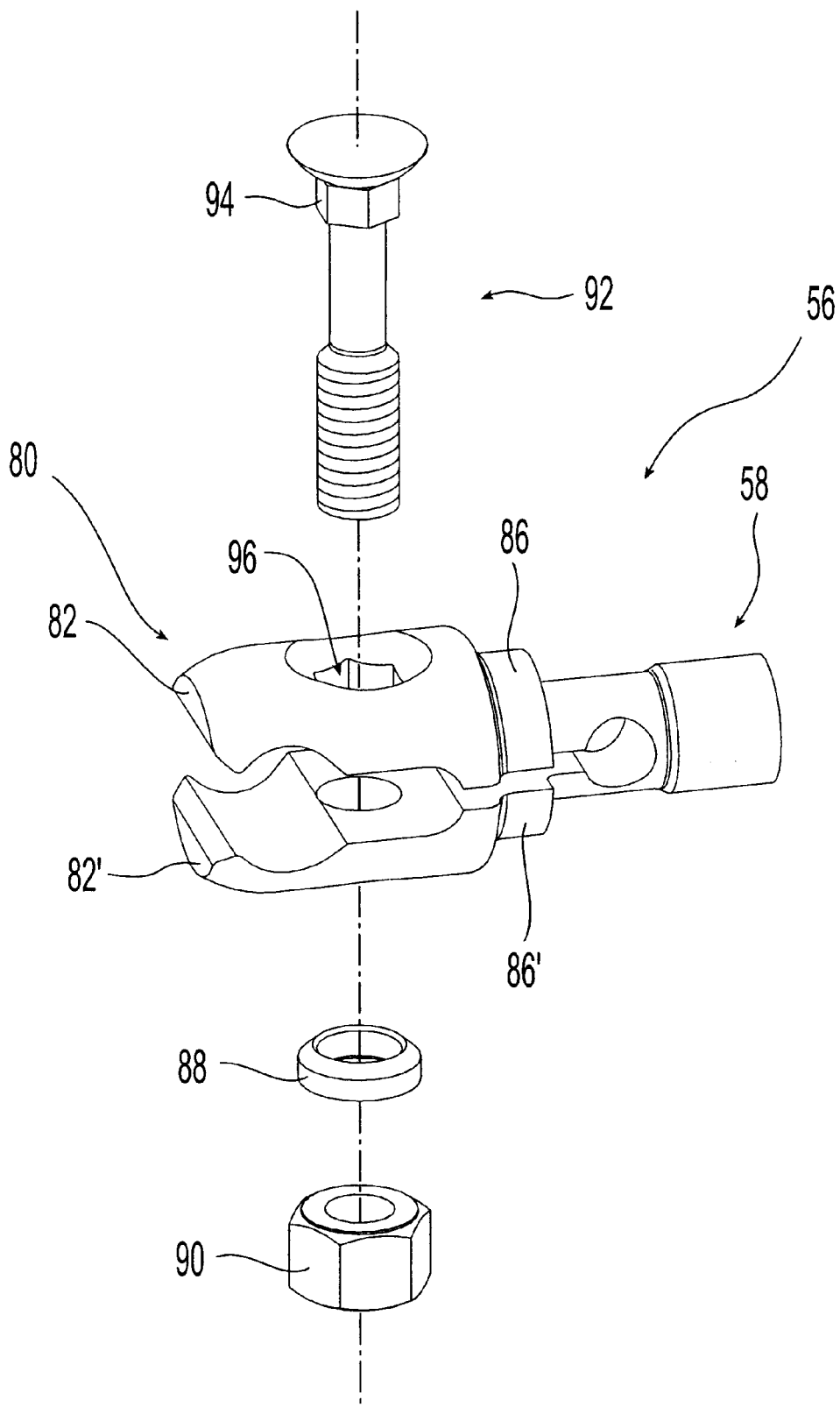
FIG. 4 is an exploded perspective view of the single piece fixation rod clamp.
Figure 5:
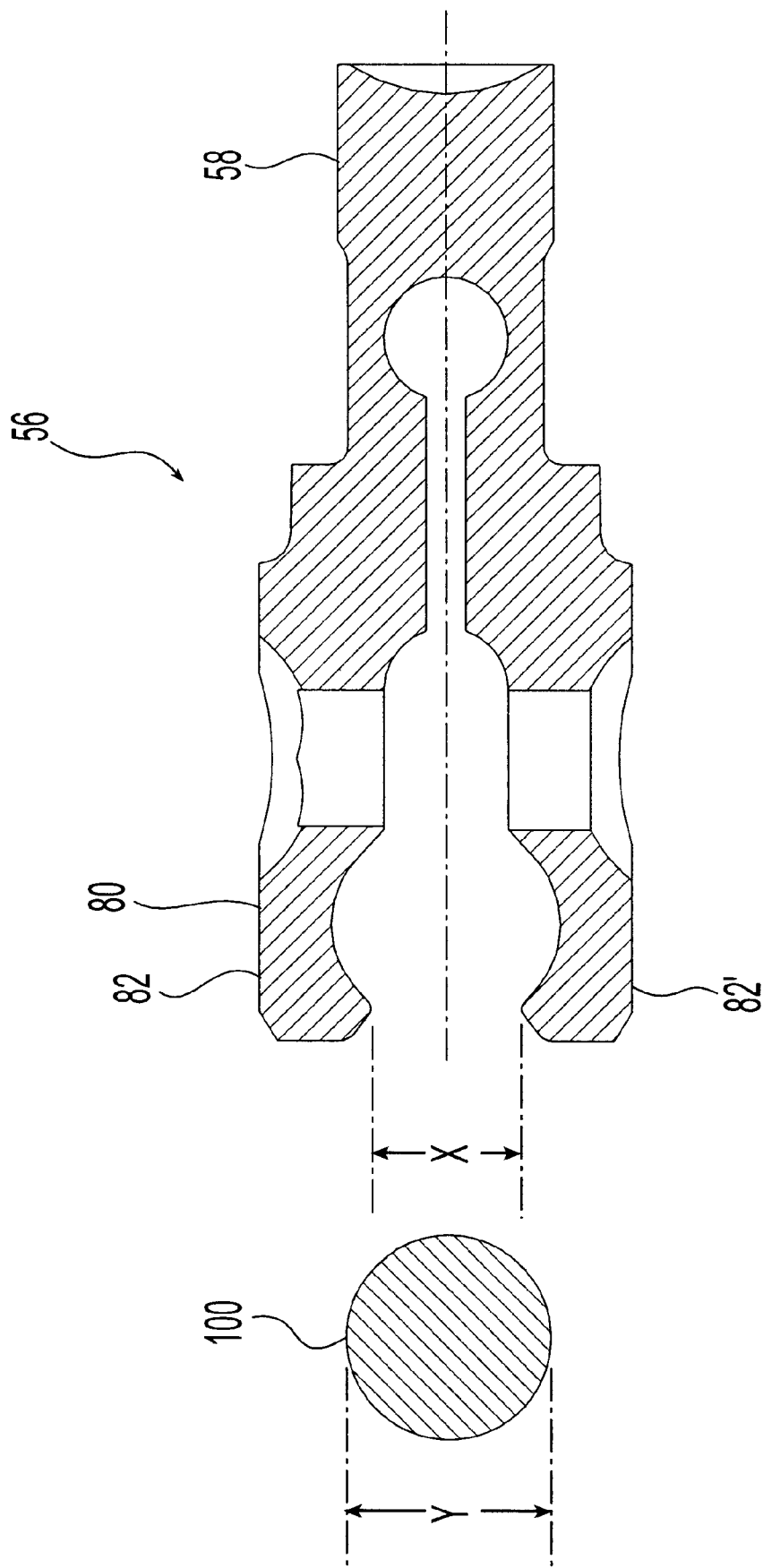
FIG. 5 is a cross-sectional view of the single-piece fixation rod clamp and a bone fixation rod.

FIG. 4 shows the details of the novel single-piece fixation rod clamp 56 of the present invention. The single-piece fixation rod clamp comprises a jaw portion 80, which further comprises a set of opposing jaws 82 and 82', each connected to a respective spring arm 86 and 86'. The spring arms converge to a smooth cylindrical coupling portion 58. Significantly, the jaw portion 80 is manufactured in a single piece, so that when the jaws 82 and 82' are positively displaced with respect to their rest position, a resulting spring force is generated which tends to force the jaws back to the rest position. The jaw portion 80 is preferably manufactured such that the initial clearance "X" between opposing jaws 82 and 82' is slightly smaller than the outside diameter "Y" of the bone fixation rod 100 (shown in FIG. 5). In this way an interference is established between jaws 82 and 82' and the bone fixation rod 100 when the bone fixation rod is initially installed into the jaw portion 80. Based on the natural spring action of the spring arms 86 and 86' adjoining the jaws 82 and 82' respectively, the relative interference between the jaws and the bone fixation rod enables the entire bone pin locking assembly (comprising pin vise portion 1 and rod attachment portion 50) to be snapped onto the bone fixation rod 100 by the operator, resulting in the capture of the bone fixation rod 100 within the rod attachment jaw portion 80. Although not fully stabilized, the spring action of the spring arms is sufficient to maintain a loose coupling of the assembly with the rod. This frees up the hands of the surgeon performing the fixation procedure.

Final stabilization of the bone fixation rod 100 within the jaw portion 80 is accomplished through the use of a bolt 92 placed through the jaw portion spring arms 86 and 86', in combination with a nut 90 (see FIG. 4). Upon tightening the nut 90 and bolt 92, the spring arms 86 and 86', and most importantly for the purposes of the invention, the adjoining jaws 82 and 82', are drawn together until the bone fixation rod 100 is firmly held between the jaws 82 and 82'. Repeated loosening and tightening of the rod attachment portion on the bone fixation rod is possible without the need for re-engagement of the rod within the jaw. In this way the surgeon may easily and multiply adjust the position of the rod attachment portion along the bone fixation rod.

An external hexagon 94 may be provided integral to the shoulder of the jaw bolt 92. This external hexagon 94 conforms to an internal hexagonal recess 96 provided within jaw portion spring arm 86. The bolt is thereby rotationally fixed to the jaw portion, such that the surgeon need only focus on threading the nut onto the bolt without having to worry about holding the bolt still.

A washer 88 may be provided between the nut 90 and jaw portion spring arm 86'. This washer can be of any design known in the art satisfactory to prevent galling of the nut and jaw portion spring arm, and to facilitate installation of nut 90 and bolt 92.

Figure 7:
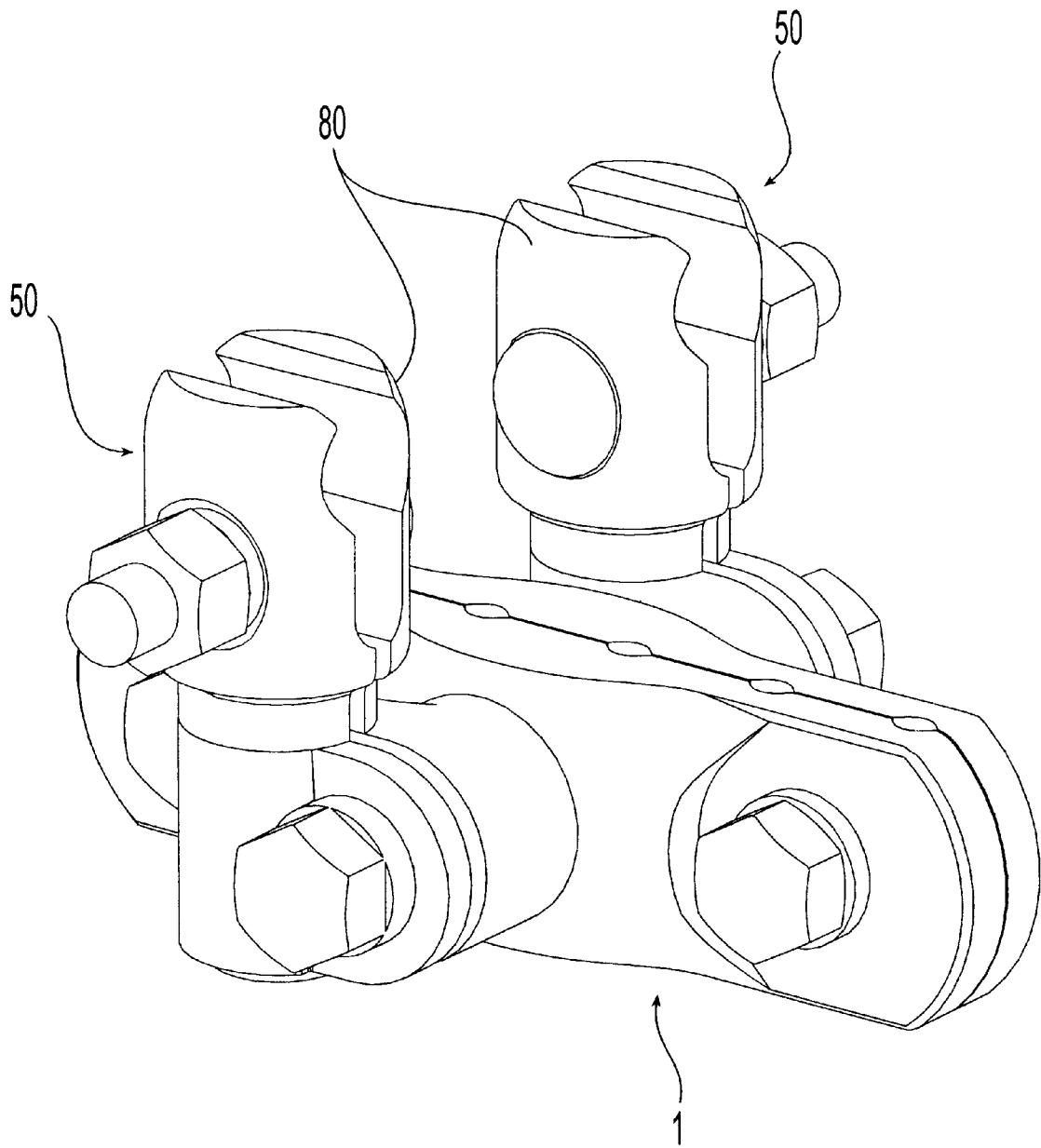
FIG. 7 is a perspective view of the stacked clamp assembly embodiment of the present invention.

FIG. 7 shows a "stacked" bone pin locking assembly which comprises one pin vise portion 1 with two associated rod attachment portions 50. Such a stacked assembly permits the surgeon to provide an additional stabilizing force, associated with a second bone fixation rod 100, to the fracture site. In this way a framework of bone fixation rods may be built about the fracture site.

Accordingly, it should be understood that the embodiments disclosed herein are merely illustrative of the principles of the invention. Various other modifications may be made by those skilled in the art which will embody the principles of the invention and fall within the spirit and the scope thereof.

What is claimed is:

1. An external fixator for reducing fragments of a bone comprising:
    a bone fixation rod having a longitudinal axis and two ends,
    at least two sets of bone pins, each set comprising at least one bone pin, and each bone pin having a proximal end and a distal end, the distal end being insertable into bone on either side of a fracture, and
    a bone pin locking assembly for use with the bone fixation rod and bone pins, the assembly comprising:
        a pin vise portion comprising first and second engaging faces, capable of engaging the proximal ends of the bone pins, and
        a rod attachment portion comprising:
            a single-piece fixation rod clamp having a jaw portion, a coupling portion and a longitudinal axis,
            a coupling having a rod clamp cooperating portion and a pin vise cooperating portion,
    wherein the jaw portion of the single-piece fixation rod clamp permits engagement of the bone fixation rod when the single-piece fixation rod clamp is pressed onto the bone fixation rod, thereby mechanically coupling the bone pin locking assembly to the bone fixation rod.

2. The external fixator of claim 1 wherein the assembly is capable of being immobilized along the bone fixation rod without freedom to rotate or move.

3. The external fixator of claim 2 further comprising a bolt disposed within and operatively associated with the single-piece fixation rod clamp jaw portion, wherein immobilization is achieved by the tightening of the bolt.

4. The external fixator of claim 1 wherein the single-piece fixation rod clamp jaw portion comprises first and second opposing jaws having a clearance therebetween which is sufficient to provide an interference between the opposing jaws and bone fixation rod when the bone fixation rod is initially inserted into the single-piece fixation rod clamp jaw portion.

5. The external fixator of claim 4, further comprising first and second spring arms, wherein the first opposing jaw connects to the first spring arm, and the second opposing jaw connects to the second spring arm, such that when the first and second opposing jaws are positively displaced from a rest position, a resulting spring force is generated which forces the jaws back to the rest position.

6. The external fixator of claim 4, further comprising first and second spring arms, wherein the first opposing jaw connects to the first spring arm, and the second opposing jaw connects to the second spring arm, such that when at least one of the first and second opposing jaws is positively displaced from a rest position, a resulting spring force is generated in the corresponding spring arm, urging the displaced jaw back toward the rest position.

7. The external fixator of claim 6 wherein when the bone fixation rod is inserted into the single-piece fixation rod clamp jaw portion, the spring force contributes to the mechanical coupling of the bone pin locking assembly to the bone fixation rod.

8. The external fixator of claim 1 wherein the single-piece fixation rod clamp jaw portion engages the bone fixation rod when the single-piece fixation rod clamp is pressed onto the bone fixation rod in a direction substantially along the single-piece fixation rod clamp longitudinal axis.

9. The external fixator of claim 1 wherein the single-piece fixation rod clamp jaw portion engages the bone fixation rod when the single-piece fixation rod clamp is pressed onto the bone fixation rod in a direction substantially perpendicular to the longitudinal axis of the bone fixation rod.

10. An external fixator for reducing fragments of a bone comprising:
    a bone fixation rod having a longitudinal axis and two ends,
    at least two sets of bone pins, each set comprising at least one bone pin, with each bone pin having a proximal end and a distal end, the distal end being insertable into bone on either side of a fracture, and
    a bone pin locking assembly for use in an external fixator system with the bone fixation rod and bone pins, the assembly comprising:
        a pin vise portion comprising first and second engaging faces, capable of engaging the proximal ends of the bone pins, and
        a rod attachment portion comprising:
            a single-piece fixation rod clamp having a jaw portion, a coupling portion and a longitudinal axis,
            a rotatable coupling with a rod clamp cooperating portion and a pin vise cooperating portion, the coupling allowing: (i) rotation of the single-piece fixation rod clamp about a first axis substantially perpendicular to the pin vise portion engaging faces, and (ii) rotation of the single-piece fixation rod clamp about the rod clamp longitudinal axis, the rod clamp longitudinal axis being substantially perpendicular to the first axis, wherein the jaw portion of the single-piece fixation rod clamp permits engagement of the bone fixation rod when the single-piece fixation rod clamp is pressed onto the bone fixation rod, thereby mechanically coupling the bone pin locking assembly to the bone fixation rod.

11. The external fixator of claim 10 wherein the assembly is capable of being immobilized along the bone fixation rod without freedom to rotate or move.

12. The external fixator of claim 11 further comprising a bolt disposed within and operatively associated with the single-piece fixation rod clamp jaw portion, wherein immobilization is achieved by the tightening of the bolt.

13. The external fixator of claim 10 wherein the single-piece fixation rod clamp jaw portion comprises first and second opposing jaws having a clearance therebetween which is sufficient to provide an interference between the opposing jaws and bone fixation rod when the bone fixation rod is initially inserted into the single-piece fixation rod clamp jaw portion.

14. The external fixator of claim 13 further comprising first and second spring arms, wherein the first opposing jaw connects to the first spring arm, and the second opposing jaw connects to the second spring arm, such that when the first and second opposing jaws are positively displaced from a rest position, a resulting spring force is generated which forces the jaws back to the rest position.

15. The external fixator of claim 11, further comprising first and second spring arms, wherein the first opposing jaw connects to the first spring arm, and the second opposing jaw connects to the second spring arm, such that when at least one of the first and second opposing jaws is positively displaced from a rest position, a resulting spring force is generated in the corresponding spring arm, urging the displaced jaw back toward the rest position.

16. The external fixator of claim 15 wherein when the bone fixation rod is inserted into the single-piece fixation rod clamp jaw portion, the spring force contributes to the mechanical coupling of the bone pin locking assembly to the bone fixation rod.

17. The external fixator of claim 10 wherein the single-piece fixation rod clamp jaw portion engages the bone fixation rod when the single-piece fixation rod clamp is pressed onto the bone fixation rod in a direction substantially along the single-piece fixation rod clamp longitudinal axis.

18. The external fixator of claim 10 wherein the single-piece fixation rod clamp jaw portion engages the bone fixation rod when the single-piece fixation rod clamp is pressed onto the bone fixation rod in a direction substantially perpendicular to the longitudinal axis of the bone fixation rod.

19. The external fixator of claim 10 wherein the rotatable coupling pin vise cooperating portion comprises a bearing face incorporating serrations which cooperate with serrations in the pin vise portion, and whereupon engagement of the cooperating serrations serves to prevent relative rotational movement between the coupling portion and the pin vise portion.

20. The external fixator of claim 19, wherein the rotatable coupling pin vise cooperating portion further comprises a spring and a bore, wherein the spring is partially slidably accepted within the bore and compressed between the rotatable coupling pin vise cooperating portion and the pin vise portion, and wherein the spring provides a force tending to separate the rotatable coupling portion and the pin vise portion to allow free relative rotational movement during operation.

21. An external fixator for reducing fragments of a bone comprising:
a bone fixation rod having a longitudinal axis and two ends,
at least two sets of bone pins, each set comprising at least one bone pin, and each bone pin having a proximal end and a distal end, the distal end being insertable into the bone on either side of a fracture, and
a bone pin locking assembly for use with the bone fixation rod and bone pins, the assembly comprising:
a pin vise portion comprising first and second opposing plates, each plate having an outside face and a clamping face with grooves, the plates coupled with screw and nut combinations disposed at opposing ends of the plates, and which pin vise portion is capable of engaging the proximal ends of the bone pins through contact with grooves of the first and second plates upon tightening of the screw and nut combinations, and
a rod attachment portion comprising:
a single-piece fixation rod clamp having a jaw portion, a coupling portion and a longitudinal axis,
a rotatable coupling with a rod clamp cooperating portion and a pin vise cooperating portion, the coupling allowing: (i) rotation of the single-piece fixation rod clamp about a first axis substantially perpendicular to the pin vise portion engaging faces, and (ii) rotation of the single-piece fixation rod clamp about the rod clamp longitudinal axis, the axis being substantially perpendicular to the first axis,
wherein the jaw portion of the single-piece fixation rod clamp permits engagement of the bone fixation rod when the single-piece fixation rod clamp is pressed onto the bone fixation rod from the side of the bone fixation rod, thereby mechanically coupling the bone pin locking assembly to the bone fixation rod.

22. The external fixator of claim 21 wherein the assembly is capable of being immobilized along the bone fixation rod without freedom to rotate or move.

23. The external fixator of claim 22 further comprising a bolt disposed within and operatively associated with the single-piece fixation rod clamp jaw portion, wherein immobilization is achieved by the tightening of the bolt.

24. The external fixator of claim 21 wherein the single-piece fixation rod clamp jaw portion comprises first and second opposing jaws having a clearance therebetween which is sufficient to provide an interference between the opposing jaws and bone fixation rod when the bone fixation rod is initially inserted into the single-piece fixation rod clamp jaw portion.

25. The external fixator of claim 24 further comprising first and second spring arms, wherein the first opposing jaw connects to the first spring arm, and the second opposing jaw connects to the second spring arm, such that when the first and second opposing jaws are positively displaced from a rest position, a resulting spring force is generated which forces the jaws back to the rest position.

26. The external fixator of claim 24, further comprising first and second spring arms, wherein the first opposing jaw connects to the first spring arm, and the second opposing jaw connects to the second spring arm, such that when at least one of the first and second opposing jaws is positively displaced from a rest position, a resulting spring force is generated in the corresponding spring arm, urging the displaced jaw back toward the rest position.

27. The external fixator of claim 26 wherein when the bone fixation rod is inserted into the single-piece fixation rod clamp jaw portion the spring force contributes to the mechanical coupling of the bone pin locking assembly to the bone fixation rod.

28. The external fixator of claim 21 wherein the single-piece fixation rod clamp jaw portion engages the bone fixation rod when the single-piece fixation rod clamp is pressed onto the bone fixation rod in a direction substantially along the single-piece fixation rod clamp longitudinal axis.

29. The external fixator of claim 21 wherein the single-piece fixation rod clamp jaw portion engages the bone fixation rod when the single-piece fixation rod clamp is pressed onto the bone fixation rod in a direction substantially perpendicular to the longitudinal axis of the bone fixation rod.

30. The external fixator of claim 21 wherein the pin vise portion clamping face grooves comprise arcuate cutouts for contacting the bone pins along less than 180 degrees of the circumference of the bone pins upon tightening of the screw and nut combinations.

31. The external fixator of claim 21 wherein the pin vise portion clamping face grooves comprise cutouts of triangular cross section, capable of contacting the bone pins along less than 180 degrees of the circumference of the bone pins.

32. The external fixator of claim 21 wherein the pin vise portion clamping face comprises a plurality of grooves capable of engaging the proximal ends of the bone pins, wherein the grooves are disposed along the pin vise clamping faces between the vise bolts disposed at opposing ends of the first and second opposing plates.

* * * * *